(12) United States Patent
Sherwood et al.

(10) Patent No.: US 12,042,431 B2
(45) Date of Patent: Jul. 23, 2024

(54) GLAUCOMA DRAINAGE IMPLANT VENTING ASSEMBLY

(71) Applicant: UNIVERSITY OF FLORIDA RESEARCH FOUNDATION, INC., Gainesville, FL (US)

(72) Inventors: Mark B. Sherwood, Gainesville, FL (US); Craig Allen Meyers, Trenton, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 885 days.

(21) Appl. No.: 17/050,267

(22) PCT Filed: May 2, 2019

(86) PCT No.: PCT/US2019/030370
§ 371 (c)(1),
(2) Date: Oct. 23, 2020

(87) PCT Pub. No.: WO2019/213377
PCT Pub. Date: Nov. 7, 2019

(65) Prior Publication Data
US 2021/0106462 A1    Apr. 15, 2021

Related U.S. Application Data

(60) Provisional application No. 62/667,057, filed on May 4, 2018.

(51) Int. Cl.
*A61F 9/007*        (2006.01)

(52) U.S. Cl.
CPC .. *A61F 9/00781* (2013.01); *A61F 2220/0075* (2013.01)

(58) Field of Classification Search
CPC ............................ A61F 9/00781; A61F 9/007
See application file for complete search history.

(56) References Cited

U.S. PATENT DOCUMENTS 5,338,291 A    8/1994   Speckman et al.
5,626,558 A *   5/1997   Suson ................. A61F 9/00781
                                                                     604/9

(Continued)

OTHER PUBLICATIONS

International Searching Authority, International Search Report and Written Opinion for International Application No. PCT/US2019/030370, Jul. 12, 2019, (8 pages), U.S. Patent and Trademark Office, USA.

*Primary Examiner* — Nicholas J. Weiss
*Assistant Examiner* — Priyadharshi Seetharaman
(74) *Attorney, Agent, or Firm* — Alston & Bird LLP

(57) ABSTRACT

Provided herein is a glaucoma drainage implant assembly. The assembly may include a drainage implant tube defining a lumen there through defining a fluid channel between an anterior chamber of an eye and a region outside of the sclera of the eye; a closure disposed at a position outside the anterior chamber of the eye, the closure configured to preclude fluid flow from the anterior chamber of the eye to the region outside of the sclera of the eye; and a shunt received within the drainage implant tube, between the end of the drainage implant tube in the anterior chamber of the eye and the closure, where the shunt is configured to permit fluid flow from the anterior chamber of the eye, through the drainage implant tube, and out of the drainage implant tube external to the sclera of the eye through the shunt.

20 Claims, 3 Drawing Sheets

(56) References Cited

U.S. PATENT DOCUMENTS

| | | |
|---|---|---|
| 2001/0000527 A1 | 4/2001 | Yaron et al. |
| 2003/0135149 A1 | 7/2003 | Cullen et al. |
| 2003/0236483 A1 | 12/2003 | Ren |
| 2004/0162545 A1* | 8/2004 | Brown ................ A61F 9/00781 977/778 |
| 2007/0293872 A1 | 12/2007 | Peyman |
| 2010/0249691 A1* | 9/2010 | Van Der Mooren ........................ A61F 9/00781 604/9 |
| 2011/0105986 A1 | 5/2011 | Bronstein et al. |

* cited by examiner

GLAUCOMA DRAINAGE IMPLANT VENTING ASSEMBLY

CROSS-REFERENCE TO RELATED APPLICATIONS

This application claims priority to PCT Application No. PCT/US2019/030370, filed on May 2, 2019, which claims priority to U.S. Provisional Patent Application Ser. No. 62/667,057, filed on May 4, 2018, the contents of each of which are hereby incorporated by reference in their entirety.

FIELD OF INVENTION

The present disclosure relates to glaucoma surgical implant devices, and more particularly, allowing for effective fluid release from a glaucoma drainage implant during the initial post-operative period.

BACKGROUND

Glaucoma is a prevalent disease of the eye that can cause blindness. Aqueous humor is a liquid that is produced inside of the eye that provides nourishment to the cornea and lens, and also maintains intraocular pressure. In a normal eye, there exists a drainage path that allows aqueous humor to drain away and be absorbed by the body at a rate that is similar to the rate of its production. This results in proper intraocular pressure being maintained. Glaucoma occurs when this drainage path does not function adequately and intraocular pressure increases.

SUMMARY

An objective of this present disclosure is to provide an assembly for uniformly and repeatably allowing release of fluid from a glaucoma drainage implant tube during a period in which the fluid flow to the main plate of the glaucoma drainage implant is restricted.

An embodiment of this present disclosure includes an assembly that allows for the effective release of fluid from a glaucoma drainage implant tube. The assembly may include a drainage implant and a shunt. The drainage implant consists of a tube which is attached to a broad plate constructed of silicone, PMMA or other material. The tube of the drainage implant is open to the anterior chamber of the eye at one end and to the plate of the drainage implant at the other creating a fluid channel from the anterior chamber of the eye to the plate of the drainage implant. The shunt may be configured to be inserted through the tube wall and into the lumen of the drainage implant tube. Additionally, the shunt may be configured to at least partially define a fluid flow channel from the lumen of the drainage implant to the subconjunctival space, external to the tube.

These figures and embodiments herein are meant to illustrate and further describe the present disclosure, however these are not intended to limit any aspect of the device.

An example embodiment provided herein includes a glaucoma drainage implant assembly. The assembly may include a drainage implant tube defining a lumen there through, the drainage implant tube including a first end defining an opening to the lumen, where the first end of the drainage implant tube is configured to be received within an anterior chamber of an eye, and a second end of the drainage implant tube that is configured to be disposed outside of a sclera of the eye, the lumen providing a fluid channel from the anterior chamber of the eye to an external surface of the sclera of the eye; a closure disposed at a position between the first end of the drainage implant tube and the second end of the drainage implant tube, the closure configured to preclude fluid flow from the anterior chamber of the eye to the second end of the drainage implant tube; and a shunt received within the drainage implant tube, between the first end of the drainage implant tube and the closure, where the shunt is configured to permit fluid flow from the anterior chamber of the eye, through the first end of the drainage implant tube, and out of the drainage implant tube external to the sclera of the eye through the shunt.

According to some embodiments, the shunt may include a body, where the at least one channel is defined along a length of the body and configured to enable flow from the lumen of the drainage implant tube to a location outside of the drainage implant tube. The shunt may include a tubular body defining a cavity there through and a hole defined through the body to the cavity, where the hole is configured to allow fluid flow from the lumen of the drainage implant tube into the cavity, where the cavity is configured to carry the fluid to a location external to the drainage implant tube. The tubular body of the shunt may be configured to extend between a first end of the body outside of the drainage implant tube, through the lumen of the drainage implant tube, to a second end of the body outside of the drainage implant tube. The shunt may include a suture attached to the shunt, where the shunt may be removed from the drainage implant tube in response to a pulling force received on the suture. The hole may be between about 40 and 50 microns in diameter. The shunt may include a pointed leading edge, where the shunt may be configured to penetrate the drainage implant tube in response to the pointed leading edge being pressed into the drainage implant tube.

Embodiments described herein may provide a glaucoma drainage shunt to be received within a glaucoma drainage implant. The shunt may include: a substantially cylindrical body, where the body is configured to be received within the lumen of a drainage implant tube, the lumen in fluidic communication with an anterior chamber of an eye; a pointed end of the substantially cylindrical body may be configured to aid penetration of the glaucoma drainage implant; and a suture attached to the substantially cylindrical body at an end opposite that of the pointed end. The shunt may facilitate fluidic communication between the lumen of the drainage implant tube and a region exterior to the drainage implant tube. The substantially cylindrical body may include one or more grooves extending along the substantially cylindrical body, where the one or more grooves may define a fluid flow path along the substantially cylindrical body from the lumen of the drainage implant tube to the region exterior to the drainage implant tube. The substantially cylindrical body may define a hollow channel through the substantially cylindrical body extending longitudinally along the substantially cylindrical body. The shunt may define at least one hole through the shunt, permitting fluid communication between the lumen of the drainage implant tube and the hollow channel, where the at least one hole through the shunt and the hollow channel define a fluid flow path from the lumen of the drainage implant tube to the region exterior to the drainage implant tube.

BRIEF DESCRIPTION OF THE DRAWINGS

Some embodiments of this present disclosure may be further understood by the detailed descriptions and corresponding figures.

DETAILED DESCRIPTION

Figure 1:
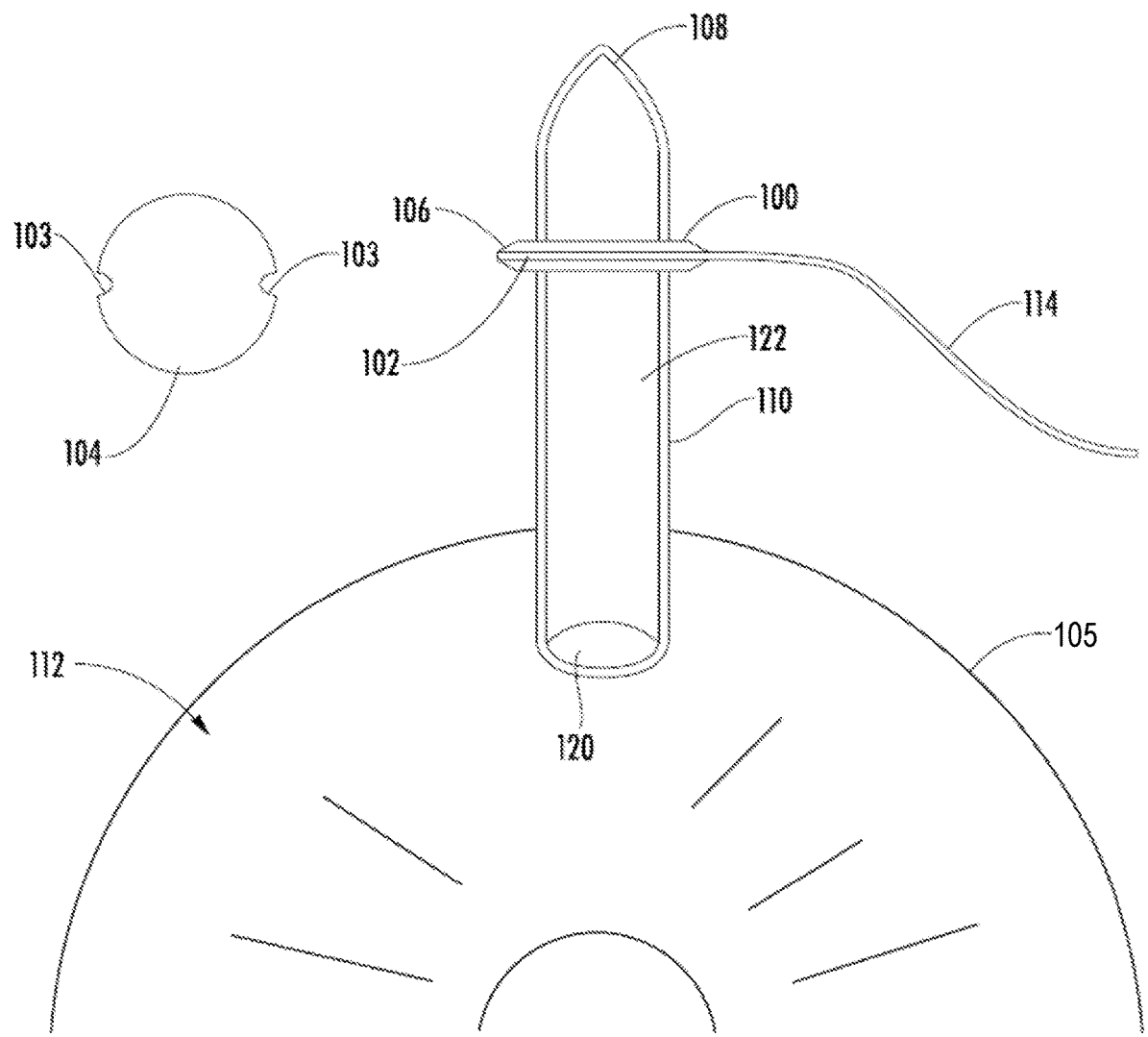
FIG. 1 illustrates a glaucoma drainage implant assembly including a shunt according to an example embodiment of the present invention.

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements.

As noted above, glaucoma is a prevalent disease of the eye that can lead to blindness. Aqueous humor is a fluid produced within the eye that drains through a drainage path, and is absorbed by the body at a rate similar to the rate of production of the fluid. The production of aqueous humor and the natural drainage in a healthy eye results in an intraocular pressure of around 10 to 21 millimeters of mercury (mm-Hg) being maintained. When natural drainage of the eye is diminished or precluded, intraocular pressure may increase and lead to glaucoma. Pharmaceuticals may be used to treat and regulate intraocular pressure. However, when pharmaceuticals are not sufficient, surgery may be necessary.

Surgery to relieve intraocular pressure often involves placing an implant under the conjunctiva, the tissue that covers the white of the eye and lines the inside of the eyelids. The purpose of the implant is to create a drainage pathway for the aqueous humor to relieve pressure within the eye and maintain an intraocular pressure approximating the pressure within a healthy eye, of about 10 to 21 mm-Hg. Conventionally, glaucoma drainage implants include a flexible glaucoma drainage device that is implanted in the eye to divert aqueous humor from inside the eye to an location external to the sclera (white of the eye), underneath the conjunctiva. These implants may include a small tube which may, for example, be made of a silicone material, which is open at one end and attached to a plate or drainage element at the end of the tube opposite the open end. The open end of the tube portion of the implant is inserted into the anterior chamber of the eye, while the drainage element is placed on the surface of the sclera (the white of the eyeball) under the conjunctiva. Excess aqueous humor is then permitted to flow from the open end of the tube disposed within the anterior chamber of the eye to the drainage element of the implant at a controlled rate, and absorbed through the tissues of the eye, thereby regulating the intraocular pressure.

Once the implant is placed in the eye, the body begins to form a tissue capsule around the implant. The structure of this tissue capsule is very important as its permeability is key to the rate at which the fluid from inside the eye can be dispersed. The capsule takes several weeks to fully develop. During this time excessive aqueous fluid can pass up the tube which can lead to intraocular pressures which are too low. To prevent the early over drainage the tube is frequently occluded with a blocking stitch. While this blocking stitch is in place the intraocular pressure can remain too high.

In example procedures using the constricting suture or other flow-restricting methods, after the tissue capsule forms some time later, the constricting stitch is removed allowing aqueous humor to flow to the drainage element of the implant. However, during the time it takes for the capsule to form, the elevated pressure in the eye still needs to be relieved. Presently, when a surgeon restricts the aqueous humor through the tube of the implant with a constricting suture, the surgeon may create one or more holes or slits in the tube in an effort to allow some aqueous humor to leak from the tube thereby temporarily relieving the pressure in the eye. Such procedures are typically free-hand and the results are clinically highly variable. Further, even when the slits or holes are consistently cut with a template, machine, or other repeatable, controllable mechanism, the tube material may cause variation in the resultant hole or slit. Further, the slit made in the tube material may not adequately open, eliminating the perceived benefit of the slit.

Through applied effort, ingenuity, and innovation, the problem of effectively releasing fluid from the drainage implant therefore relieving intraocular pressure after implantation of the implant tube and constricting suture or other closure mechanism has been solved by developing solutions that are included in embodiments of the present invention, examples of which are described in detail herein.

Embodiments described herein involve placing a small, substantially rigid shunt through the tube of the drainage device. The shunt may include a small (e.g., #32 Birmingham gauge) hollow stainless steel tube with a small hole bored through a wall of the shunt. This shunt can be inserted through the implant tube and advanced until the hole of the shunt is located in the lumen of the implant tube. The shunt then functions to regulate the intraocular pressure by allowing aqueous humor to flow through the hole in the wall of the shunt located within the implant tube, and through the end of the shunt, located outside of the implant tube. The shunt may remain in place until the capsule is sufficiently formed around the tube within the eye. The constricting stitch and the shunt may then be removed to allow the fluid to flow through the tube to the drainage element of the glaucoma drainage device. Further, embodiments may include shunts having different profiles and different mechanisms for permitting fluid flow from the lumen of the implant tube to outside of the implant tube.

FIG. 1 is an illustration of an embodiment of an assembly configured to allow fluid to flow from the lumen 122 of the drainage implant tube to an exterior region (while the drainage tube is closed off 108) via a depression 102 in the body of the shunt 100 in order to regulate intraocular pressure by providing consistent and appropriate flow of fluid. The assembly represented in FIG. 1 is shown as already implanted into an eye 105 with an opening 120 of the drainage implant located in the anterior chamber 112 of the eye.

The implant tube includes a casing 110 defining a wall of the tube. The casing 110 may be a number of different types of material. In a preferred embodiment, the casing 110 is silicone. The casing 110 defines an opening 120 that allows for fluid to enter into a lumen 122, or cavity, of the drainage implant tube.

The opening 120 of the drainage implant tube casing 110 may be placed in the anterior chamber 112 of the eye in order to allow fluid to enter through the opening 120 and into the lumen 122. Conventionally, the lumen would extend to the drainage element (not shown) of the drainage implant thereby allowing fluid to flow from the anterior chamber 112 of the eye 105 to the drainage element and away from the eye. However, as described above, the tube may be occluded using a closure stitch or other mechanism to "pinch off" the drainage implant tube 108 and preclude fluid flow through the lumen 122 to the drainage element.

As illustrated in FIG. 1, the drainage implant tube casing 110 is occluded at 108. This occluded state may be desirable during the early stages of implantation to prevent early excessive low pressure in the eye and to allow the tissue capsule to form appropriately. The occluded portion of the tube 108 may be occluded in a number of different ways. In a preferred embodiment, the occluded portion 108 is occluded by at least one closure suture or an internal suture in the tube lumen and an external tightening suture around the tube.

According to the illustrated embodiment, in order for fluid to exit the lumen 122 when the drainage implant tube casing 110 is occluded at 108, a shunt 100 is inserted through the casing 110 at least partially into the lumen 122 of the drainage implant tube to provide a fluid flow channel from the lumen 122 of the drainage implant tube to a region external to both the sclera of the eye 105 and the drainage implant tube lumen 122. The shunt 100 may be fabricated from a number of different types of material. In a preferred embodiment, the shunt 100 is stainless steel.

Penetration of the casing 110 of the drainage implant tube by the shunt 100 may be performed in a number of ways, including manually by a human or mechanically by a machine or device.

In an example embodiment, the shunt 100 may include a pointed end 106 to allow easier penetration of the casing 110 of the drainage implant tube. In an example embodiment, the end of the shunt 100 opposite a pointed end 106 may have a suture 114 attached. The suture 114 may allow for easier removal of the shunt 100 from the drainage implant tube.

Some examples of the shunt 100 penetrating the drainage implant tube are included in the present disclosure, however, the shunt 100 may penetrate the casing 110 in any number of ways. According to an example embodiment, the shunt may only penetrate the casing 110 once and stop at a point within the lumen 122 of the drainage implant enough so that the shunt 100 provides a fluid flow channel to a region external to the drainage implant tube. In another exemplary embodiment, the shunt 100 may penetrate the casing 110 twice in order to provide a fluid flow channel to a region external to the drainage implant tube.

It would be obvious to one skilled in the art that the shunt 100 is not required to create its own opening through the casing 110 in response to being pressed through the casing of the drainage implant tube. For example, at least one opening may be created on the casing 110 of the drainage implant to allow the shunt 100 to be inserted through the at least one opening, allowing the shunt 100 to provide a fluid flow channel to a region external to the drainage implant tube. Such an opening in the casing 110 may be created manually (e.g., using a template or free-hand), using a machine (e.g., laser cut, mechanical punch, etc.) or by the leading tip of the implant itself.

FIG. 1 represents an embodiment of the present disclosure wherein the shunt 100, when inserted at least partially through the casing 110 of a drainage implant tube provides a fluid flow channel from the lumen 122 of the drainage implant tube to a region external to the sclera of the eye 105 and the drainage implant tube by way of at least one depression 102 in the body of the shunt 100. The fluid groove 102 may extend from at least one end of the body of the shunt 100. In a preferred embodiment, the fluid groove (s) 102 may extend in a straight line or in a spiral fashion along a longitudinal axis of the body from one end of the body of the shunt 100 to an opposite end. FIG. 1 provides a cross-section view 104 of the shunt 100, wherein two depressions 103 are defined in the body of the shunt 100 and extend from one end of the shunt 100 to the other end of the shunt 100.

Figure 2:
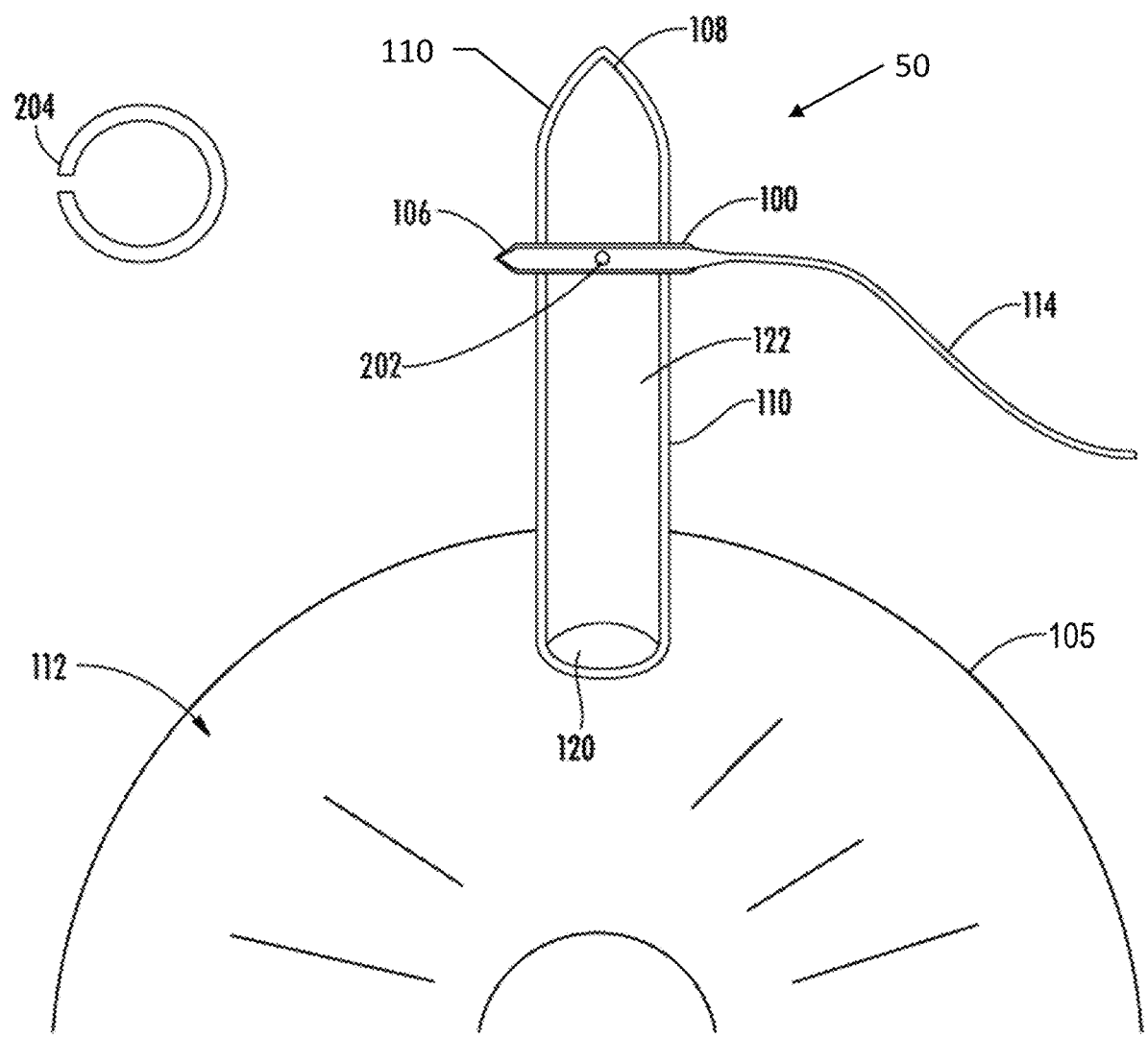
FIG. 2 illustrates a glaucoma drainage implant assembly including a shunt according to another example embodiment of the present invention.

FIG. 2 represents another example embodiment of the present disclosure wherein the shunt 100 is hollow with openings on both ends of the shunt 100 thereby defining a cavity within the shunt 100. According to the illustrated embodiment, the shunt 100 includes at least one opening 202 in the body of the shunt 100 in fluidic communication with the cavity of the shunt 100. FIG. 2 provides a cross-section view 204 of the shunt where at least one opening 202 is present in the body of the shunt allowing fluid to flow from the lumen 122 of the drainage implant tube, through the opening 202 and through the hollow cavity of the shunt to a region external to the eye and the drainage implant tube. The opening 202 of various embodiments may be of a size configurable by a user. For example, the opening 202 may be sized appropriately for the drainage necessary from the eye. According to some embodiments, the opening 202 may be between approximately 30 microns and 60 microns.

According to example embodiments described herein, shunts, grooves 102 and/or openings 202 may be sized and shaped according to a desired flow rate of aqueous humor from the drainage implant tube to a region external to the drainage implant tube. A shunt configured as shown in FIG. 2 may include one opening 202 or a plurality of openings, and the openings may be of specifically configured sizes to permit a precise volume of fluid flow based on the intraocular pressure exhibited. Shunts may be of different sizes and configurations to allow a surgeon to select a shunt of a particular flow rate based on patient needs. For example, a patient experiencing a high degree of intraocular pressure may require a shunt with a higher flow rate (e.g., more openings 202 or larger openings 202) than a patient experiencing a lower degree of intraocular pressure. Shunts configured according to the type shown in FIG. 1 may also be sized according to desired flow rate through the size and/or number of channels 103 extending along a body of the shunt 100. Further, a shunt may be configured to be adjustable, whereby a size or number of openings 202 through the shunt 100 may be configurable to enable a surgeon to "dial in" or fine tune a flow rate through a shunt based on the characteristics of a particular patient's eye.

Embodiments described herein may enable a uniform flow rate of aqueous humor from a drainage implant tube during a period in which the drainage implant tube is closed off precluding fluid flow through the tube.

Figure 3:
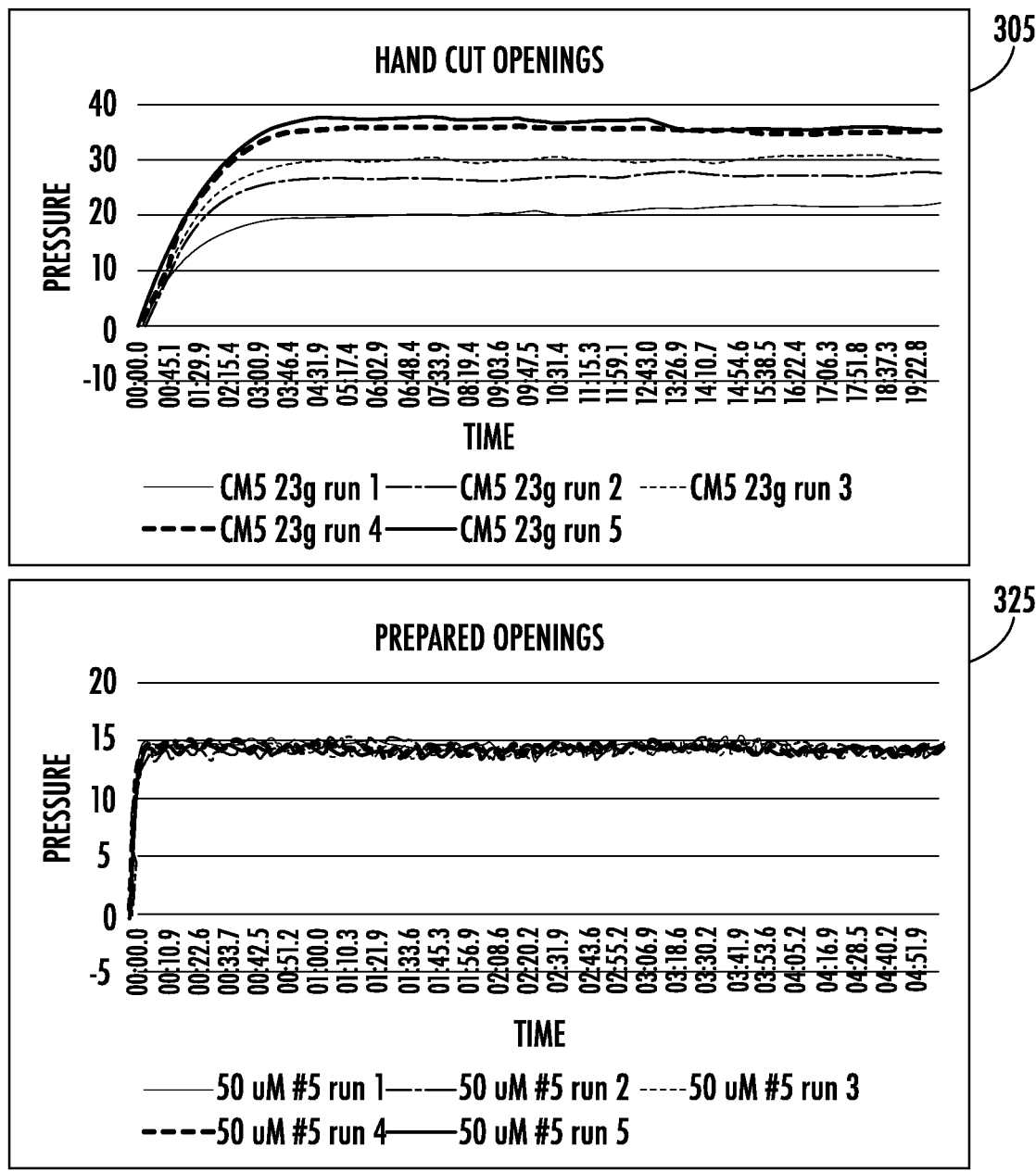
FIG. 3 illustrates pressure plots of intraocular pressure resulting from drainage using example embodiments described herein relative to conventional drainage methods.

FIG. 3 illustrates an example embodiment of the improvement of the consistency of drainage of aqueous humor through the tube of an implant with a constricting suture. An initial study was performed where openings or slits were manually cut in an implant tube (e.g., tube 110 of FIG. 1 or 2) using a 23 gauge blade in a silicone implant tube. Using manual cutting of the openings or slits, substantial variation existed in the drainage rate of the aqueous humor, not only among different operators making the incisions, but also among the incisions themselves. Plot 305 of FIG. 3 illustrates an example embodiment of the variation of pressure due to the flow of aqueous humor when openings were manually made. Plot 325 of FIG. 3 illustrates the resultant pressure based on flow rates of several trial runs using example embodiments described herein in which openings through which aqueous humor is drained are machine cut or laser cut. As shown, using example embodiments described herein, consistent flow rates of aqueous humor draining from the implant tube may be achieved, particularly when compared against the variability experienced using manually cut holes or incisions. Having a more consistent and repeatable flow rate enables the flow of aqueous humor to be regulated from the eye to reduce pressure within the eye while not draining too much or too little. This enables pressure to be maintained in a safe range while promoting the health of a patient.

Any modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A glaucoma drainage implant assembly comprising:
    a drainage implant tube defining a lumen there through, the drainage implant tube comprising a first end defining an opening to the lumen, wherein the first end of the drainage implant tube is configured to be received within an anterior chamber of an eye, and wherein a second end of the drainage implant tube opposite the first end is configured to be disposed outside a sclera of the eye, the lumen providing a fluid channel from the anterior chamber of the eye to external surface of the sclera of the eye;
    a closure disposed at a position between the first end of the drainage implant tube and the second end of the drainage implant tube, the closure configured to preclude fluid flow from the anterior chamber of the eye to the second end of the drainage implant tube; and
    a shunt received within the drainage implant tube, between the first end of the drainage implant tube and the closure, wherein the shunt is configured to permit fluid flow from the anterior chamber of the eye, through the first end of the drainage implant tube, and out of the drainage implant tube external to the sclera of the eye through the shunt, wherein the shunt extends through a side of the drainage implant tube.

2. The assembly of claim 1, wherein the shunt comprises a body, wherein the at least one channel is defined along a length of the body configured to enable fluid flow from the lumen of the drainage implant tube to a location outside of the drainage implant tube.

3. The assembly of claim 1, wherein the shunt comprises a tubular body defining a cavity there through, and a hole defined through the body to the cavity, wherein the hole is configured to allow fluid flow from the lumen of the drainage implant tube into the cavity, wherein the cavity is configured to carry the fluid to a location external to the drainage implant tube.

4. The assembly of claim 3, wherein the tubular body of the shunt is configured to extend between a first end of the body outside of the drainage implant tube, through the lumen of the drainage implant tube, to a second end of the body outside of the drainage implant tube.

5. The assembly of claim 4, wherein the shunt further comprises a suture attached to the shunt, wherein the shunt is removed from the drainage implant tube in response to a pulling force received on the suture.

6. The assembly of claim 3, wherein the hole is between about 40 microns and 50 microns in diameter.

7. The assembly of claim 1, wherein the shunt comprises a pointed leading edge, wherein the shunt is configured to penetrate the drainage implant tube in response to the pointed leading edge being pressed into the drainage implant tube.

8. A glaucoma drainage shunt to be received within a glaucoma drainage implant, the shunt comprising:
    a substantially cylindrical body, wherein the body is configured to be received within a lumen of a drainage implant tube, the lumen in fluidic communication with an anterior chamber of an eye;
    a pointed end of the substantially cylindrical body configured to aid penetration of the glaucoma drainage implant; and
    a suture attached to the substantially cylindrical body at an end opposite that of the pointed end.

9. The glaucoma drainage shunt of claim 8, wherein the shunt facilitates fluidic communication between the lumen of the drainage implant tube and a region exterior to the drainage implant tube.

10. The glaucoma drainage shunt of claim 9, wherein the substantially cylindrical body comprises one or more grooves extending longitudinally along the substantially cylindrical body, wherein the one or more grooves defines a fluid flow path along the substantially cylindrical body from the lumen of the drainage implant tube to the region exterior to the drainage implant tube.

11. The glaucoma drainage shunt of claim 9, wherein the substantially cylindrical body defines a hollow channel through the substantially cylindrical body extending longitudinally along the substantially cylindrical body and at least one hole through the shunt, permitting fluid communication between the lumen of the drainage implant tube and the hollow channel, wherein the at least one hole through the shunt and the hollow channel define a fluid flow path from the lumen of the drainage implant tube to the region exterior to the drainage implant tube.

12. The glaucoma drainage implant assembly of claim 1, wherein the shunt is configured to permit fluid flow from the anterior chamber of the eye while the closure precludes fluid flow through the second end of the drainage implant tube.

13. The glaucoma drainage implant assembly of claim 1, wherein the shunt is received within the drainage implant tube across a width of the drainage implant tube.

14. The glaucoma drainage implant assembly of claim 13, wherein the shunt comprises a body, wherein the at least one channel is defined along a length of the body configured to enable fluid flow from the lumen of the drainage implant tube, through a side of the lumen, to a location outside of the drainage implant tube.

15. A glaucoma drainage implant assembly comprising:
    a drainage implant tube defining a lumen there through, the drainage implant tube comprising a first end defining an opening to the lumen, wherein the first end of the drainage implant tube is configured to be received within an anterior chamber of an eye, and wherein a second end of the drainage implant tube is configured to be disposed outside a sclera of the eye, the lumen providing a fluid channel from the anterior chamber of the eye to external surface of the sclera of the eye;

a closure disposed at a position between the first end of the drainage implant tube and the second end of the drainage implant tube, the closure configured to preclude fluid flow from the anterior chamber of the eye to the second end of the drainage implant tube; and a shunt received within the drainage implant tube transverse to an axis along which the drainage implant tube extends, between the first end of the drainage implant tube and the closure, wherein the shunt is configured to permit fluid flow from the anterior chamber of the eye, through the first end of the drainage implant tube, and out of the drainage implant tube external to the sclera of the eye through the shunt.

16. The glaucoma drainage implant assembly of claim 15, wherein the shunt comprises a tubular body defining a cavity there through, and a hole defined through the body to the cavity, wherein the hole is configured to allow fluid flow from the lumen of the drainage implant tube into the cavity, wherein the cavity is configured to carry the fluid to a location external to the drainage implant tube.

17. The glaucoma drainage implant assembly of claim 16, wherein the tubular body of the shunt is configured to extend between a first end of the body outside of the drainage implant tube, through the lumen of the drainage implant tube, to a second end of the body outside of the drainage implant tube.

18. The glaucoma drainage implant assembly of claim 15, wherein the shunt comprises a pointed leading edge, wherein the shunt is configured to penetrate the drainage implant tube in response to the pointed leading edge being pressed into the drainage implant tube.

19. The glaucoma drainage implant assembly of claim 15, wherein the shunt is configured to permit fluid flow from the anterior chamber of the eye while the closure precludes fluid flow through the second end of the drainage implant tube.

20. A glaucoma drainage implant assembly comprising:
a drainage implant tube defining a lumen there through, the drainage implant tube comprising a first end defining an opening to the lumen, wherein the first end of the drainage implant tube is configured to be received within an anterior chamber of an eye, and wherein a second end of the drainage implant tube opposite the first end is configured to be disposed outside a sclera of the eye, the lumen providing a fluid channel from the anterior chamber of the eye to external surface of the sclera of the eye;

a closure disposed at a position between the first end of the drainage implant tube and the second end of the drainage implant tube, the closure configured to preclude fluid flow from the anterior chamber of the eye to the second end of the drainage implant tube; and a shunt received within the drainage implant tube, between the first end of the drainage implant tube and the closure, wherein the shunt is configured to permit fluid flow from the anterior chamber of the eye, through the first end of the drainage implant tube, and out of the drainage implant tube external to the sclera of the eye through the shunt, wherein the shunt comprises a pointed leading edge, wherein the shunt is configured to penetrate the drainage implant tube in response to the pointed leading edge being pressed into the drainage implant tube.

* * * * *